United States Patent
Alabata et al.

(10) Patent No.: US 8,992,996 B2
(45) Date of Patent: *Mar. 31, 2015

(54) COSMETIC

(71) Applicant: Restorsea, LLC, New York, NY (US)

(72) Inventors: Enrique P. Alabata, Torrance, CA (US); Patricia S. Pao, New York, NY (US)

(73) Assignee: Restorsea, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/904,501

(22) Filed: May 29, 2013

(65) Prior Publication Data

US 2014/0072547 A1    Mar. 13, 2014

Related U.S. Application Data

(63) Continuation-in-part of application No. PCT/US2013/022728, filed on Jan. 23, 2013.

(60) Provisional application No. 61/589,592, filed on Jan. 23, 2012.

(51) Int. Cl.
| | | |
|---|---|---|
| A61K 35/54 | (2006.01) | |
| A61K 8/92 | (2006.01) | |
| A61K 35/60 | (2006.01) | |
| A61K 8/64 | (2006.01) | |
| A61Q 19/00 | (2006.01) | |
| A61K 8/97 | (2006.01) | |
| A61K 8/66 | (2006.01) | |
| A61K 8/36 | (2006.01) | |
| A61K 8/63 | (2006.01) | |
| A61Q 19/08 | (2006.01) | |
| A61K 8/98 | (2006.01) | |

(52) U.S. Cl.
CPC .............. *A61K 8/922* (2013.01); *A61K 35/60* (2013.01); *A61K 8/64* (2013.01); *A61Q 19/00* (2013.01); *A61K 8/97* (2013.01); *A61K 8/66* (2013.01); *A61K 8/92* (2013.01); *A61K 8/361* (2013.01); *A61K 8/63* (2013.01); *A61Q 19/08* (2013.01); *A61K 8/987* (2013.01)
USPC ........... 424/558; 424/94.3; 424/581; 424/401

(58) Field of Classification Search
None
See application file for complete search history.

(56) References Cited

U.S. PATENT DOCUMENTS

| | | | |
|---|---|---|---|
| 6,346,245 B1 | 2/2002 | Walther et al. | |
| 6,551,606 B1 | 4/2003 | Golz-Berner et al. | |
| 6,592,866 B2 | 7/2003 | Walther et al. | |
| 6,716,450 B1 | 4/2004 | Yin et al. | |
| 6,846,485 B2 | 1/2005 | Bjarnason | |
| 7,094,415 B2 | 8/2006 | Marenick | |
| 7,829,081 B2 | 11/2010 | Bookbinder et al. | |
| 8,075,920 B2 | 12/2011 | Gammelsaeter et al. | |
| 8,460,713 B2 | 6/2013 | Gammelsaeter et al. | |
| 8,557,295 B2 | 10/2013 | Gammelsaeter et al. | |
| 2002/0064857 A1 | 5/2002 | Walther et al. | |
| 2005/0129739 A1 | 6/2005 | Kohn et al. | |
| 2005/0163872 A1* | 7/2005 | Khare ..................... | 424/748 |
| 2006/0073211 A1 | 4/2006 | Marenick et al. | |
| 2006/0105005 A1 | 5/2006 | Marenick et al. | |
| 2008/0161229 A1 | 7/2008 | Matsunaga et al. | |
| 2009/0274770 A1 | 11/2009 | Gammelsaeter et al. | |
| 2011/0020302 A1 | 1/2011 | Banov et al. | |
| 2011/0027327 A1 | 2/2011 | Albrecht | |
| 2011/0280882 A1 | 11/2011 | Walther et al. | |
| 2012/0082695 A1* | 4/2012 | Asam ..................... | 424/195.17 |
| 2012/0123442 A1 | 5/2012 | Larsen et al. | |
| 2012/0309689 A1 | 12/2012 | Leren et al. | |
| 2013/0028947 A1 | 1/2013 | Albrecht | |
| 2013/0129742 A1 | 5/2013 | Walther et al. | |
| 2013/0261063 A1 | 10/2013 | Gammelsaeter et al. | |
| 2013/0336948 A1 | 12/2013 | Alabata et al. | |
| 2014/0037752 A1 | 2/2014 | Gammelsaeter et al. | |
| 2014/0072547 A1 | 3/2014 | Alabata et al. | |
| 2014/0220088 A1 | 8/2014 | Walther et al. | |

FOREIGN PATENT DOCUMENTS

| | | | |
|---|---|---|---|
| JP | 2009207473 | | 9/2009 |
| JP | 201065048 | | 3/2010 |
| KR | 20080059066 | | 6/2008 |
| WO | 9929836 | | 6/1999 |
| WO | WO 2010/042399 | * | 4/2010 |
| WO | 2010049688 | | 5/2010 |
| WO | WO 2010/049688 A1 | * | 5/2010 |
| WO | WO 2011/006508 | * | 1/2011 |
| WO | 2011064384 | | 6/2011 |
| WO | 2011135059 | | 11/2011 |
| WO | 2012175742 | | 12/2012 |

(Continued)

OTHER PUBLICATIONS

Hare (SA Pharmacist's Assistant (Summer 2007) p. 30).*

(Continued)

*Primary Examiner* — Susan Hoffman

(74) *Attorney, Agent, or Firm* — Fish & Richardson P.C.

(57) ABSTRACT

A composition is provided that includes a fish spawn protein isolate. A natural product extract is also present that includes unsaturated fatty acids and sterols. An emulsifier is provided to form a mixture of the isolate and the extract. A composition is also provided that includes an egg hatching protein isolate and at least one biocide protective of isolate activity. An emulsifier forms a mixture with the isolate that has an aqueous phase buffered to a pH of between 5.6 and 7.9. A process of producing such a cosmetic has an emulsion or an aqueous phase that is buffered to a pH of between 5.5 and 7.9 prior to the addition of isolate to the emulsion. A process of improving skin appearance is provided that includes the application of the cosmetic to the skin at least three times per week to achieve the improvement of the skin appearance.

23 Claims, No Drawings

(56) References Cited

FOREIGN PATENT DOCUMENTS

| WO | 2012175743 | 12/2012 |
|---|---|---|
| WO | 2013112569 | 8/2013 |
| WO | 2014091312 | 6/2014 |
| WO | 2014094918 | 6/2014 |
| WO | 2014096187 | 6/2014 |

OTHER PUBLICATIONS

"Omega-3,6, and 9 and How They Add Up" (http://www.uccs.edu/Documents/peakfood/hlthTopics/Omega-3_6_and_9_Fats.pdf)—accessed Oct. 31, 2013.*

Karasakal (Planta Med (2011), vol. 77, pp. PA28).* http://plants.usda.gov/core/profile?symbol=LOJA—accessed Oct. 31, 2013.*

Screenshot of shopping4net.se/Haelsokost/Vaard-hygien/Salvor/Zona-Sensitive.htm (machine translation) Nov. 7, 2007.

Screenshot of http://nordicexpressions.org/z_skin_repair.htm; Nov. 26, 2013.

Screenshot of http://www.apothekenbote.at/zona-sensitive-creme-75ml.html (machine translation); Jul. 2007.

Screenshot of http://www.amil.com.pl/?id=25&mod=&tpl=&_action= (machine translation) Aug. 12, 2009.

Screenshot of nordicexpressions.org/zona.htm ZSkinRepairSeries1.pdf Oct. 31, 2007, 'The Z Skin Repair Series for problem skin'.

Screenshot of nordicexpressions.org/zona.htm ZSkinRepairSeries2.pdf Oct. 31, 2007, 'Z Skin Repair and Zonase—a patented solution for problem skin'.

Screenshot of nordicexpressions.org/zona.htm ZSkinRepairSeries3.pdf Oct. 31, 2007, 'Z Skin Repair Extra Intensive Cream'.

Screenshot of nordicexpressions.org/zona.htm ZSkinRepairSeries4.pdf Oct. 31, 2007, 'Z Skin Repair Kids Sensitive Cream'.

Screenshot of nordicexpressions.org/zona.htm ZSkinRepairSeries5.pdf Oct. 31, 2007, 'Z Skin Repair Shampoo'.

Screenshot of nordicexpressions.org/zona.htm ZSkinRepairSeries6.pdf Oct. 31, 2007, 'Z Skin Repair Scalp Lotion Spray'.

Screenshot of nordicexpressions.org/zona.htm ZSkinRepairSeries7.pdf Oct. 31, 2007, 'Z Skin Repair Hand & Nail Cream'.

Screenshot of nordicexpressions.org/zona.htm ZSkinRepairSeries8.pdf Oct. 31, 2007, 'Z Skin Repair Lip Balm'.

Wei Bai et al., Toxicity of zinc oxide nanoparticles to zebrafish embryo: a physicochemical study of toxicity mechanism; J Nanopart Res (2010) 12:1645-1654.

Natasha M. Franklin et al.Comparative Toxicity of Nanoparticulate ZnO, Bulk ZnO, and ZnCl2 to a Freshwater Microalga (*Pseudokirchneriella subcapitata*): The Importance of Particle Solubility; Environ. Sci. Technol. 2007, 41, 8484-8490.

Screenshot of http://www.mediconline.se/hudvard/problemhud/zona-byter-namn-till-z-skin-repair-c-160-1.aspx (machine translation) Sep. 30, 2011.

Lonne GK et al., Composition Characterization and Clinical Efficacy Study of a Salmon Egg Extract, International Journal of Cosmetic Science 35(5):515-22, Oct. 2013.

Coste F, Multi-functional Marine Active Ingredient as a Gentle Alternative to AHAs, http://www.google.com/url?url=http://www.in-cosmetics.com/novadocuments/11186&rct=j&frm=1&q=&esrc=s&sa=U&ei=avsRVPLIMM6PyASAIILABg&ved=0CC0QFjAl&sig2=nytjK8ymfCWZGJGhNxrEdA&usg=AFQjCNGWxmhHbdcOMJ0pjVA1-xwC26FF0w, Apr. 2012, p. 9,10,25.

Warner AH, Matheson C, Release of Proteases from Larvae of the Brine Shrip *Artemia franciscana* and Their Potential Role During the Molting Process, Comp. Biochem. Physiol. B-Biochem. Mol. Biol. 119(2):255-63, Feb. 1998.

Z Skin Repair Intensive Cream Electi Medicals, <http://www.halsans.com/en/body-care/skin-hair-nail-products/z-skin-repair-intensive-cream/>; <http://nordicexpressions.org/z_skin_repair.htm>, Sep. 2014.

The Restorsea 3-Step Regimen, http://www.restorsea.com/info/Regimen_Offer#tabs, Jul. 1, 2014.

Blue Plasma, http://www.perriconemd.com/productiblue+plasma.do, Oct. 7, 2012.

Lex—Ground Breaking Natural Multifunctional Technology for Age Management and Improvement of Skin Appearance, http://www.regenics.no/filer/cosmetics.htm, Mar. 4, 2013.

Valeria Orsetti, thesis: "Molecular Studies of Piscine Hatching Enzymes", http://tesi.cab.unipd.it/14043/1/Orsetti_Valeria.pdf, 2007.

Yasumasu et al., "Isolation and Some Properties of Low Choriolytic Enzyme (LCE), a Component of the Hatching Enzyme of the Teleost, *Oryzias latipes*," J. Biochem., 105, p. 212-218, 1988.

Warner et al., "Water Disrupts Stratum Corneum Lipid Lamellae; Damage is Similar to Surfactants," J. Invest. Dermatol. 113:960-966, 1999.

Wang et al., "Total phenolic compounds, radical scavenging and metal chelation of extracts from Icelandic seaweeds," Food Chemistry 116: 240-248, 2009.

Cho et al., "The Antioxidant Properties of Brown Seaweed (*Sargassum siliquastrum*) Extracts,"J Med Food 10:479-485, 2007.

Biotechmarine (R), "Kalpariane (R)", www.labo-esthesante.fr/minexcell28/pdf/7726_2.pdf, Aug. 13, 2008.

AA2G stabilised vitamin C from Hayashibara. Hayashibara International, Inc., Apr. 1, 2003.

Prospectus of Aqua Bio Technology ASA; Dec. 2007.

Bedford, Robert F., NDA 19-617/S027—Diprivan (propofol) Injectable Emulsion Apr. 26, 1996.

* cited by examiner

COSMETIC

CROSS-REFERENCE TO RELATED APPLICATIONS

This application is a non-provisional application that claims priority benefit of as a continuation-in-part of PCT Application Serial Number PCT/US2013/022728, filed Jan. 23, 2013; that in turn claims priority benefit of U.S. Provisional Application Ser. No. 61/589,592, filed Jan. 23, 2012 the contents of which are hereby incorporated by reference.

FIELD OF THE INVENTION

The present invention in general relates to the cosmetic and components thereof, and in particular to a cosmetic containing egg hatching proteinaceous extracts and formulations thereof that are useful to enhance skin quality.

BACKGROUND OF THE INVENTION

Traditional cosmetic formulations have included oils and various lipophilic substances that formulate a protective coating on skin to mitigate weathering effects. The inclusion of a sunblock in a cosmetic also mitigates ultraviolet damage to the skin associated with aging and free radical production. Other components conventional to cosmetic compositions are emollients that convey appreciable quantities of water to the skin that in combination with oils affects the amount of moisture released or retained from skin to mask wrinkles. Unfortunately, such conventional cosmetic formulations have failed to afford a long term, chemical improvement of skin quality.

The observation of fish hatchery workers whose hands had exceptional skin quality even with prolonged exposure to cold water was the genesis of the isolation of a new class of proteins associated with fish eggs. Such proteins are detailed for example in U.S. Pat. Nos. 6,346,245; 6,592,866; U.S. 2011/0280882; WO2011/06434; and U.S. 2009/0274770. The proteins so isolated included zonases, leukolectins, very acidic proteins (VAPS) and choroelysins. At least some of these proteins are effective in treating autoimmune and inflammatory disorders, as well as damaged skin, all with minimal side effects. While such proteins improved damaged skin function associated with weathering and various environmental stressors, such as exposure to air conditioning or airborne pollutants, these proteins appear to have little or no effect on other attributes associated with damaged and aged skin. Additionally, while the inclusion of such fish spawn isolate proteins in cosmetics has been contemplated, the ability to maintain protein activity and afford storage stability in a cosmetic formulation represents a technical challenge.

Thus, there exists a need for a storage stable cosmetic that treats multiple aspects of skin aging while incorporating the anti-inflammatory attributes of eggs and in particular, fish spawn derived proteins. There further exists a need for such a cosmetic that is essentially free of synthetic cosmetic components that have unintended deleterious effects on the skin and bioaccumulation problems.

SUMMARY OF THE INVENTION

A composition is provided that includes a fish spawn protein isolate having an anti-inflammatory effect on mammalian skin. A natural product extract is also present that includes unsaturated fatty acids and sterols. The natural product extract has anti-oxidant activity. An emulsifier or a solubilizer, or a combination thereof is provided to form a mixture of the isolate and the extract. A composition is also provided that includes an egg hatching protein isolate having an anti-inflammatory effect on mammalian skin. At least one biocide protective of activity of the egg hatching protein isolate for 3 months storage at 20° C. is present while the activity when applied to subject skin after storage remains within 80% of unformulated and freshly isolated protein. An emulsifier forms a mixture with the egg hatching protein isolate that has an aqueous phase buffered to a pH of between 5.6 and 7.9. A kit is provided inclusive of an aforementioned composition in a non-sterile, multi-use package along with instructions for the application thereof to skin to promote skin rejuvenation.

A process of producing a cosmetic inclusive of an egg hatching protein isolate having activity on the skin of a mammal includes the formation of at least one aqueous phase and at least one hydrophobic phase. An emulsifier and the at least one biocide are present in at least one of the at least one aqueous phase and the at least one hydrophobic phase. The at least one aqueous phase and the at least one hydrophobic phase are combined to form an emulsion. The emulsion or the at least one aqueous phase is buffered to a pH of between 5.5 and 7.9 prior to the addition of the egg hatching protein isolate to the emulsion.

A process of improving skin appearance is provided that includes the application of the composition to the skin of a mammal at a level of from $1\times10^{-6}$ to 0.1 mg of the isolate and $2\times10^{-7}$ to 0.02 mg of the unsaturated fatty acids per square cm of skin at least three times per week to achieve the improvement of the skin appearance.

DESCRIPTION OF THE INVENTION

The present invention has utility as a cosmetic with skin restorative attributes. In one embodiment, an inventive cosmetic is formulated to afford a synergistic effect between various components. In yet another embodiment, an inventive cosmetic composition is formulated absent synthetic components. An inventive cosmetic in all embodiments maintains the activity of proteinaceous components while having storage stability at ambient temperature and in response to microbial challenge through non-sterile processing and subject usage microbial contamination. A process of formulation is provided that affords a cosmetic formulation with these attributes of maintained protein activity and storage stability under the conditions of cosmetic usage and storage.

According to the present invention, egg hatching active proteins and in particular, fish spawn isolated protein having anti-inflammatory effect on living mammalian skin is combined with a natural product extract including unsaturated fatty acids and at least one sterol. The extract simultaneously has anti-oxidant activity and collagenase inhibition activity and is combined with an emulsifier that stabilizes the mixture including the protein isolate and the extract. It is appreciated that multiple extracts are optionally used herein simultaneously to achieve the compositional and activity requirements. It has been surprisingly found that the activity of egg hatching proteins, and in particular fish spawn protein and natural product extract operate synergistically in some inventive embodiments to achieve superior appearance to skin and in some embodiments skin rejuvenation, as compared to either ingredient used alone in a controlled formulation. In still other embodiments, storage stability of an inventive cosmetic of at least 3 months at 20° C. is provided while the protein component activity when applied to subject skin after storage remains within 80% of unformulated and freshly isolated protein.

A fish spawn protein isolate for example, includes a zonase, a leukolectin, or a combination thereof and has the properties detailed in U.S. Pat. No. 6,346,245, col. 4, line 15-col. 5, line 8; U.S. 2009/0274770 A1 [0321]-[0326] and U.S. 2011/0280882 [0157]-[0194]; crude extracts containing such proteins; and combinations thereof. Exemplary sources of fish spawn for protein isolation include roes from sturgeon, salmon, whitefish, vendace, cod, capelin, and burbot. It is appreciated that other sources of egg proteins operative herein include amphibian egg cases; such as those of tadpoles, and salamanders; reptilian egg cases; fowl egg cases; invertebrate eggs such as of starfish, sea urchins, and crabs. Typically, an egg- or with particularity, fish spawn protein-isolate containing at least some of the above recited proteins constitutes from 0.0001 to 10% total weight of an inventive cosmetic formulation with 0.01 to 10 percent of the extract being active protein. It is appreciated that the amount of protein present in an inventive cosmetic depends on factors illustratively including miscibility with other components of another cosmetic, and degree of skin damage.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

An inventive composition also contains a natural product extract. The natural product extract includes an unsaturated fatty acid and a sterol in an amount to provide an anti-oxidant activity and collagenase inhibition activity of greater than 10% relative to the control, as measured by Oxygen Radical Absorbance Capacity (ORAC) testing and tracer of lipoperoxidation in culture medium with a natural product extract present at 1% and radiated with ultraviolet B in an amount of 150 millijoules per square centimeter, respectively. R. L. Prior, et al. Assays for Hydrophillic and Lipophillic Antioxidant Capacity (oxygen radical absorbance capacity (ORAC$_{FL}$)) of Plasma and other Biological and Food Samples. J. Agric. Food Chem. (2003) 51:3273-3279. It is appreciated that natural extracts often contain mixtures of unsaturated fatty acids, one or more sterols, and other components of varying dermatological activity. An product extract used in an inventive composition also inhibits collagenase activity in some embodiments by more than 5% in some embodiments as measured against a control for a 0.1% by weight extract in the control through a protocol of visual measurement of anti-collagenase testing on human biopsies with cyro skin slices being incubated 30 minutes at 37° C. with, and without an extract followed by three hours of incubation at 37° C. without (negative control) or with 15 microliters per milliliter collagenase followed by rinsing of the biopsy samples followed by coloration and microscopy for visual measurement of trichome of Masson. In some embodiments, a natural product extract used in an inventive composition includes at least one of an omega-3, an omega-6, and omega-9 fatty acids. In still other embodiments, the unsaturated fatty acids are present in the natural product extract in an amount of at least 20 milligrams per 100 grams of extract. An inventive natural product extract also includes at least one type of sterol, the sterol illustratively including cholesterol, campesterol, stigmasterol, sitosterol, hydroxylated forms thereof and combinations thereof. In some embodiments, the at least one sterol is present in a natural product extract in an amount of greater than 50 milligrams per 100 grams of extract. Typically, a natural product extract is present in inventive composition from 0.01 to 10 total weight percent and in some embodiments from 0.1 to 3 total weight percent. Factors determinative in selecting the quantity of natural product extract illustratively include stabilization of cosmetic egg hatching proteins and glucosides in the presence of egg hatching proteins, degree of skin of damage, and cosmetic shelf-life.

A natural product extract according to the present invention is readily formed by conventional techniques such as extracting a portion of a plant such as leaves, stems, buds, roots, fruit, or combinations thereof with a first solvent that is either hydrophilic or hydrophobic and filtering the mixture after being in contact with the solvent for times of from 1 to 48 hours with the quantity of solvent typically being between 1 and 20 volumes relative to that of the plant material. Extraction in solvents of decreasing hydrophilicity and elution by conventional techniques allows one to produce and inventive natural product extract. Representative fatty acid/sterol extraction techniques are found in J. S. O'Brien and A. A. Benson, J. Lipid Res., 5, 1964, pp. 432-436. The organic solvent illustratively including ethers, furans, petroleum distillates, alkanes, halogenated alkanes, alcohols, acetates, and combinations thereof. After sufficient interaction between the phases, of typically between 20 minutes and 48 hours, the organic phase is isolated to obtain an extract according to the present invention. Suitable sources of extracts include red, green, brown algaes and tuft-forming cyanobacteria collectively referred to herein as "seaweed", and plants or components thereof having purple, red, black, or orange fruits or leaf colorations where leaf coloration is measured in the presence or absence of chlorophyll. Seaweeds represent a common source of inventive natural product extracts with high levels of unsaturated fatty acids and sterols. It is appreciated that synthetic and/or animal sources of unsaturated fatty acids and sterols are readily used in an inventive composition.

In addition to the egg hatching protein isolate and the natural product extract, the inventive composition in some embodiments includes one or more other components commonly employed in cosmetics with the proviso that these components maintain the attributes of the egg hatching protein isolate and natural product extract are maintained. Representative of conventional cosmetic components that are readily formulated herewith illustratively include deionized water optionally constituting the majority by weight of the inventive cosmetic; solids and waxes such as petroleum, lanolin, ceresin, microcrystalline wax, carnuba wax, $C_{10}$-$C_{30}$ fatty acids, $C_{10}$-$C_{30}$ alcohols; oils such as olive oil, jojoba oil, castor oil, sunflower oil, hazelnut oil, shea butter, and safflower oil; viscosity modifiers/stabilizers such as guar gum, xanthan gum, carrageenan, hydroxyethyl cellulose, sclerotium gum, carbomers, polyacrylates, and acrylate-$C_{10}$-$C_{30}$ alkyl acrylate copolymers; hydrophilic moisturizers such as glycerin, propanediol, sodium lactate, sodium PCA; emollients such as dicaprylyl ether, myristyl myristate, $C_{10}$-$C_{30}$ caprates, $C_{10}$-$C_{30}$, triglycerides containing caprylic and/or capric acids, and $C_{10}$-$C_{30}$ glycerides; co-emulsifiers such as cetyl alcohol, stearyl alcohol, glyceryl stearate, stearic acid, glycol stearate, and glyceryl distearate; emulsifiers such as nonionic surfactants and anionic surfactants illustratively including salts of lauroyl lactylate, caproyl lactylate, cocoyl lactylate, stearoyl lactylate, cetearyl olivate, sorbitan olivate, glyceryl oleate citrate where typical cations include sodium, potassium, ammonium, calcium, and magnesium; silicone oils; colorants such as inorganic accompaniments and inorganic dyes; metal soap-treated or silicon-treated inorganic or organic pigments and organic dyes; non-ionic surfactants, polysiloxanes; water preservatives; pH modifiers; vitamins and vitamin metabolites such as vitamin E, vitamin K, or B vitamin complexes; essential oils; ultraviolet light absorbing compounds; fragrances; humectants; blood flow enhancing agents; agents inducing a cold sensation; antiperspirants; actives, and biocides.

As used herein an active is defined as an organic compound applied to the human skin for cleansing, beautifying, promoting attractiveness, or altering the appearance that has efficacy in improving skin attributes regardless of whether the compound is polar or non-polar in nature. As used herein, this term specifically excludes an egg hatching protein, mixture of egg hatching proteins, and the natural product extract. Active organic compounds operative herein illustratively include additional extracts such as those of the mushroom mpo Songyi, *Acacia farnesiana, Euterpe oleracea, Malpighia glabra, Bixa orellana, Prunus dulcis, Aloe vera, Rhododendron ferrugineum, Amaranthus caudatus, Angelica archangelica, Pimpinella anisum, Malus domestica, Mentha suaveolens, Oat avenanthramide, Prunus armeniaca, Arnika montana, Cynara scolymus, Asparagus officinalis, Persea americana, Cardiospermum halicacabum, Melissa officinalis, Bambusa vulgaris, Musa paradisiaca, Adansonia digitata, Berberis vulgaris, Ocimum basilicum, Laurus nobilis, Epilobium angustifolium, Allium ursinum, Geum urbanum, Betula pubescens, Quassia amara, Nigella sativa, Ribes nigrum, Moms nigra, Raphanus sativus, Camellia sinensis, Rubus fruticosus, Iris versicolor, Vaccinium myrtillus, Borago officinalis, Vicia faba, Menyanthes trifoliata, Fagopyrum esculentum, Arctium lappa, Ruscus aculeatus, Theobroma cacao, Acorns calamus, Carum carvi, Elattaria cardamomum, Daucus carota sativus, Erythroxylum catuaba, Centaurium erythraea, Matricaria chamomilla, Prunus cerasus, Cicer arietinum, Chlorella vulgaris, Aronia melanocarpa, Cinchona pubescens, Cinnamomum verum, Syzygium aromaticum, Cocos nucifera, Coffea arabica, Plectranthus barbatus, Tussilago farfara, Symphytum officinale, Plantago major, Coriandrum sativum, Zea mays, Papaver rhoeas, Centaurea cyanus, Gossypium herbaceum, Vaccinium vitis-idaea, Primula veris, Vaccinium macrocarpon, Cucumis sativus, Curcuma longa, Bellis perennis, Rosa damascena, Turnera diffusa, Taraxacum officinale, Phoenix dactylifera, Lamium album, Rosa canina, Hylocereus undatus, Daemonorops draco, Echinacea angustifolia, Leontopodium alpinum, Sambucus nigra, Acanthopanax senticosus, Phyllanthus emblica, Eucalyptus globulus, Oenthera biennis, Helichrysum arenarium, Euphrasia rostkoviana, Trigonella foenum-graecum, Ficus carica, Linum usitatissimum, Plumeria alba, Fumaria officinalis, Rumex acetosa, Gardenia Yessminoides, Gentiana lutea, Zingiber officinale, Ginkgo biloba, Panax ginseng, Solidago virgaurea, Vitis vinifera, Citrus paradisi, Camellia sinensis, Paullinia cupana, Graminis flos, Corylus avellana, Lawsonia inermis, Hibiscus sabdariffa, Lonicera japonica, Humulus lupulus, Aesculus hippocastanum, Equisetum arvense, Sempervivum tectorum, Hyssopus officinalis, Cetraria islandica, Baptisia tinctoria, Chondrus crispus, Hedera helix, Jasminum officinale, Simmondsia chinensis, Juniperus communis, Anthyllis vulneraria, Kigelia africana, Actinidia chinensis, Pueraria lobata, Alchemilla vulgaris, Lavandula angustifolia, Citrus limon, Cymbopogon cytratus, Glycyrrhiza glabra, Lilium candidum, Citrus aurantifolia, Tilia cordata, Nelumbo nucifera, Macadamia ternifolia, Magnolia biondii, Berberis aquifolium, Malva sylvestris, Mangifera indica, Calendula officinalis, Castanea sativa, Althaea officinalis, Filipendula ulmaria, Cucumis melo, Silybum marianum, Panicum miliaceum, Colophospermum mopane, Sorbus aucuparia, Verbascum thapsus, Guazuma ulmifolia, Myrtus communis, Tropaeolum majus, Azadirachta indica, Urtica dioica, Ascophyllum nodosum, Myristica fragrans, Quercus robur, Laminaria digitata, Avena sativa, Usnea barbata, Olea europaea, Allium cepa, Citrus sinensis, Mentha citrata, Origanum vulgare, Viola tricolor, Carica papaya, Capsicum annuum, Petroselinum crispum, Passiflora incarnata, Prunus persica, Pyrus communis, Centella asiatica, Paeonia officinalis, Piper nigrum, Mentha piperita, Ananas comosus, Prunus domestica, Punica granatum, Pulmonaria officinalis, Cucurbita pepo, Cydonia oblonga, Rubus idaeus, Trifolium pratense, Oryza sativa, Aspalathus linearis, Rosa centifolia, Rosmarinus officinalis, Secale cereale, Salvia officinalis, Schisandra chinensis, Hippophae rhamnoides, Sesamum indicum, Capsella bursa pastoris, Albizia julibrissin, Artemisia abrotanum, Mentha spicata, Triticum aestivum, Spirulina platensis, Picea abies, Hypericum perforatum, Averrhoa carambola, Stevia rebaudiana, Fragaria ananassa, Helianthus annuus, Melilotus officinalis, Tanacetum cinerariifolium, Citrus reticulata, Thymus vulgaris, Salvadora persica, Valeriana officinalis, Vanilla planifolia, Verbena officinalis, Viola odorata, Juglans regia, Nasturtium officinale, Citrullus lanatus, Triticum aestivum, Camellia sinensis, Crataegus rhipidophylla, Thymus serpyllum, Salix alba, Hamamelis virginia, Isatis tinctoria, Lycium barbarum, Artemisia absinthium, Achillea millefolium, Hymenaea courbaril, Cananga odorata, Tricholoma matsutake* Singer, or combinations thereof. It is appreciated that such extracts may also possess a degree of antimicrobial activity that in certain embodiments enhances the efficacy of the biocide. Active organic compounds are typically used in an inventive formulation from 0 to 1 total weight percent and in some embodiments up to 5 total weight percent. While these actives tend to be more tolerant of conventional cosmetic processing conditions and in many instances are amenable to inclusion in an aqueous or lipophilic phase distinct from the egg hatching protein and natural product extract, it should be appreciated that such active organic compounds in some embodiments are added subsequent to emulsion formation through a phase C or other separately to the emulsion.

An inventive cosmetic is readily formulated into a water-based cosmetic illustratively including a toner, a spray mist, a serum, a cream, a mask, a sunscreen, a cleanser, a moisturizer, a bath preparation, a liquid foundation, an astringent, a shaving preparation, a hair care product, and other skin care products, or a topical medicament illustratively including an anti-inflammatory agent. In particular embodiments of the present invention, a cosmetic is provided that includes a plant based emulsifier such as a lactylate that is essentially silicone-free, mineral oil-free, petrolatum-free, and free of synthetic parabens. An emulsifier "substantially free" of these compounds is defined herein as having less than 10 emulsifier weight percent of these compounds in total. An inventive formulation is readily applied to human skin in regions that specifically and illustratively include the face as a whole; the regions of the face surrounding the mouth, eyes, forehead, temples, cheeks, or chin; hand; foot; neck; scalp; elbow; chest; forearm; shoulders; legs; and combinations thereof.

An inventive cosmetic presents difficulties in formulation to maintain protein activity. In general it is observed that heating and high sheer mixing; techniques common to cosmetic formulation tend to denature the active protein. Furthermore, the active proteins are prone to microbial degradation, especially when an inventive cosmetic is processed under non-sterile conditions and stored at room temperature of 20° C. Formulation of an inventive cosmetic requires that the egg hatching protein are exposed to a limited range of pH values, sheer mixings, and heat during the process of formulation in order to maintains activity of the egg hatching protein present therein. To maintain egg hatching protein activity a process of cosmetic formulation includes the buffering of any cosmetic constituent phase to a pH of between 5.6 and 8 prior to introduction of egg hatching protein to that phase. Buffering is commonly practiced in the field and includes the addition of an acid, a base, a salt of the acid, or a combination thereof to equilibrate an aqueous solution or aqueous phase of an emulsion to a desired pH. It is appreciated that pH measurement is routine and measured quantitatively via volumetric titration or with potentiometric electrodes such as those commercially available from Thermo Fisher Scientific (Waltham Mass., USA); and qualitatively measured with litmus paper kits.

While the pH values of an inventive cosmetic being adjusted to between 5.6 and 7.9 for protein activity maintenance partially inhibit microbial degradation of egg hatching proteins, biocides are present in an inventive formulation to maintain protein activity in response to organisms present during formulation and in response to the continual seeding of the cosmetic with various microbes during usage of a multiple dose container through subject topical and respiratory contact with an inventive cosmetic. As a result, an inventive cosmetic formulation in multiple-use and storage stable formulations includes a broad spectrum biocide or a combination of biocides. A broad spectrum biocide is defined herein as having activity against Gram positive bacteria, Gram negative bacteria, and fungi associated with a healthy human subject. Biocides operative herein illustratively include benzoic acid, parabens, salicylic acid, carbolic acid, sorbic acid, alkyl p-hydroxybenzoates, p-chlorometacresol, hexachlorophene, benzalkonium chloride, chlorohexidine chloride, trichlorocarbanilide, phenoxyethanol, acylsarcosines, glutathione, malic acid, tartaric acid, ascorbic acid, ascorbates, essential plant oils, mutacin proteins, and combinations thereof. In certain embodiments of the present invention, only naturally dervied biocides are present. Naturally derived biocides illustratively include fermentation filtrates such as those of *Lactobacillus, Streptococcus mutans*, and *Leuconostoc*; bisabolol; eucalyptol; thymol; inositol; saponins; and natural extract of plants, such as Japanese honeysuckle (*Lonicera japonica*), yangti (*Rumex japonicus*), kushen (*Sophora flavescens*), candock, wild oregano, orange, sage, manifoil, common mallow, chuanxiong (*Cnidii officinale* Makino), Japanese green gentian (*Swertia japonica* Makino), bisabolol, thyme, danguii (*Angelica sinensis*), orange peel, birch, field horsetail, dishcloth gourd, horse chestnut tree, creeping saxifrage (*Saxifrage stolonifera*), arnica, lily, mugwort, peony, aloe, gardenia, as well as those detailed in M. M. Cowan, Clinical Microbiology Reviews, 12(4) October 1999, p. 564-582; or combinations thereof. Such extracts are obtained by procedures detailed in Clinical Microbiology Reviews, 12(4) October 1999, pages. 573-574 and often using a hydrophilic organic solvent such as a $C_1$-$C_8$ alcohol, polyhydric alcohols, water, and aqueous alcohols. In a specific inventive embodiment Japanese honeysuckle, phloretin (apples), galangin (*Helichrysum aureonitens*) are used as naturally derived biocides, each alone or in combination. It is appreciated that in addition to biocide properties, a natural extract often imparts a fragrance to an inventive cosmetic. A biocide is present in multi-use packages of inventive cosmetics in specific embodiments from 0.1 to 5 total weight percent. It is appreciated that quantities of biocides beyond 5 total weight percent are readily included as desired.

An inventive cosmetic is in certain embodiments pH buffered to a value of between 5.6 and 7.9 and in still other embodiments to between 6.5 and 6.8, while in still in other embodiments between 6.8 and 7.3. Without intending to be bound to a particular theory, such pH values facilitate stabilization and storage stability of the egg extract such as fish spawn isolate, and natural product extract components. The formulation of an inventive cosmetic is facilitated by pre-formulating at least two components including an oil-in-water emulsion and a second phase a water-in-oil or silicone emulsion with optional additional phases such as for example a third phase containing the active egg extract such as fish spawn isolate and/or natural product extract. Alternatively, it is appreciated that one or both of the egg hatching isolate or natural product extract are readily dispersed in either the oil-in-water emulsion, water-in-oil, water-in-silicone emulsion or a serum formulation. It has been surprisingly discovered that pH buffering of various phases prior to addition of active egg extract protein is critical in establishing storage stability for the resultant inventive cosmetic, as well as activity of the protein on subject skin.

The minority phase components of an oil-in-water emulsion illustratively include oils, waxes, esters, ethers, butters, glycerides, or combinations thereof as detailed above. The majority phase components of an oil-in-water emulsion include water, aqueous salts, humectants, and various water soluble materials as detailed above. An emulsifier for such a system include ionic surfactants, non-ionic surfactants as detailed above and also including lecithin, liposomes, and oleosomes. Other non-essential additives are readily provided as detailed above that include viscosity modifiers, emulsion stabilizers, fragrances, and the like. In specific embodiments, the oil-in-water emulsion has a pH value of 5.6 to 7.9. If certain embodiments, the oil-in-water emulsion has a pH value of 6.5 and 6.8.

The water-in-oil or water-in-silicone emulsion varies the relative quantities of minority and majority phase components and preferably relies on non-ionic surfactants and silicone derivatives as emulsifiers. Viscosity modifiers and/or emulsion stabilizers illustratively include water soluble salts, gums, waxes, and combinations thereof as detailed above. In specific embodiments, the inner phase is pH adjusted to a pH value of 5.6 to 7.9. In certain embodiments, the inner phase pH value of 6.5 to 6.8. It is appreciated that various vitamins such as vitamin E, vitamin K, ascorbic acid derivatives such as ascorbic acid glucosides are readily provided in one or both of the aforementioned emulsion phases or provided as a separate third phase.

An inventive cosmetic is readily formed by a combination of premixed phases as detailed above or alternatively all such components are intermixed in sequence conventional to the art as a unified mixture. A process of improving skin appearance is provided that includes the application of an inventive composition to the skin of a mammal at a level of from $1\times10^{-6}$ to 0.1 mg of the isolate and $2\times10^{-7}$ to 0.02 mg of the unsaturated fatty acids per square cm of skin at least three times per week to achieve the improvement of the skin appearance.

A summary of the typical ranges for inventive cosmetics are provided in Tables 1-3. It should be appreciated that other conventional base formulations are readily adjusted as detailed herein to stabilize egg hatching proteins, alone or in combination with a natural product extract containing fatty acids and sterols. A variety of conventional base formulations operative herein for a cosmetic are provided in E. W. Flick, "Cosmetic and Toiletry Formulations", $2^{nd}$ Ed., Vol. 8; 2001, Noyes Publications, Norwich, N.Y., USA (ISBN 0-1855-1454-9).

TABLE 1

Typical ranges of inventive cosmetic in oil-in water emulsion, where percentages are total weight percent. Three phase and four phase version are provided herein.

Three phase formulation

| | | |
|---|---|---|
| Phase A-1 | Deionized water | Remainder |
| | Viscosity modifier/stabilizer | 0 to 5% |
| | Hydrophilic moisturizer | 0 to 20% |
| | Vegetable oil/butter | 1 to 20% |
| | Vegetable based emollient | 0 to 20% |
| | Co-emulsifier | 0 to 10% |
| | Secondary emulsifier | 0 to 10% |
| | Lactylate emulsifier | 0.1 to 10% |
| | pH adjuster/buffer to pH 5.6 to 7.9* | 0 to 5% |
| | biocide | 0.1 to 10% |
| | fragrance | 0 to 5% |
| | non-polar active organic compounds | 0 to 1% |
| Phase B-1 | Deionized water | 1 to 20% |
| | Active (L-Ascorbic Acid 2-Glucoside) | 0 to 10% |
| | Citric Acid | 0 to 1% |
| | Sodium Citrate Dihydrate | 0 to 1% |
| | Sodium Hydroxide (20%) to pH 5.6 to 7.9 | 0 to 5% |
| | polar active organic compounds | 0 to 1% |
| Phase C-1 | active (0.034% active egg hatching protein) | 0.001 to 10 |
| | active (natural product extract) | 0.001 to 10 |

Four phase formulation

| | | |
|---|---|---|
| Phase A-2a | Deionized water | Remainder |
| | Viscosity modifier/stabilizer | 0 to 5% |
| | Hydrophilic moisturizer | 0 to 20% |
| | pH adjuster/buffer to pH 5.6 to 7.9* | 0 to 5% |
| | biocide** | 0 to 10% |
| | fragrance | 0 to 5% |
| | polar active organic compounds | 0 to 1% |
| Phase A-2b | Vegetable oil/butter | 1 to 20% |
| | Vegetable based emollient | 0 to 20% |
| | Co-emulsifier | 0 to 10% |
| | Secondary emulsifier | 0 to 10% |
| | Lactylate emulsifier | 0.1 to 10% |
| | Biocide** | 0 to 5% |
| | fragrance | 0 to 5% |
| | non-polar active organic compounds | 0 to 1% |
| Phase B-1 | Deionized water | 1 to 20% |
| | Active (L-Ascorbic Acid 2-Glucoside) | 0 to 10% |
| | Citric Acid | 0 to 1% |
| | Sodium Citrate Dihydrate | 0 to 1% |
| | Sodium Hydroxide (20%) to pH 5.6 to 7.9 | 0 to 5% |
| | polar active organic compounds | 0 to 1% |
| Phase C-1 | active (0.034% active protein) | 0.001 to 10% |
| | active (natural product extract) | 0.001 to 10% |

*pH adjustment can also be performed subsequent to combination of Phases A and B, yet prior to addition of Phase C-1.
**some quantity of biocide is required, typically 0.1 to 5 total weight percent in multi-use, non-sterile formulations.

TABLE 2

Typical ranges of inventive cosmetic in water-in-silicone emulsion, where percentages are total weight percent.

Phase A

| | |
|---|---|
| Polysiloxane | 1 to 20% |
| Other silicone | 1 to 10% |
| Silicone emulsifier/surfactant | 1 to 15% |
| Emollient (non-silicone) | 1 to 10% |
| non-polar active organic compounds | 0 to 1% |

Phase B

| | |
|---|---|
| Deionized water | remainder |
| Glycol | 1 to 30% |
| Alkali metal salt | 0.2 to 2% |
| viscosity modifier/stabilizer | 0.1 to 3% |
| pH adjuster | 0 to 3% |
| biocide** | 0 to 2% |
| polar active organic compound | 0 to 1% |

Phase C

| | |
|---|---|
| active (0.034% active protein) | 0.001 to 10% |
| active (natural product extract) | 0.001 to 10% |

TABLE 3

Typical ranges of inventive cosmetic in serum formulation, where percentages are total weight percent.

Phase A

| | |
|---|---|
| Deionized water | remainder |
| viscosity modifier | 0.1 to 2% |
| pH adjuster | 0.1 to 3% |
| Glycol | 0.01 to 10% |
| Glycerin | 0.01 to 10% |
| Biocide | 0.01 to 2% |
| polar active organic compound | 0 to 1% |

Phase B

| | |
|---|---|
| Solubilizer | 0.1 to 10% |
| non-polar active organic compound | 0 to 1% |

Phase C

| | |
|---|---|
| active (0.034% active protein) | 0.001 to 10% |
| active (natural product extract) | 0.001 to 10% |

The present invention is further illustrated with reference to the following nonlimiting examples.

EXAMPLE 1

A cosmetic cream is prepared after formulating the three phases. Phase A is heated to 75-80° C. with sufficient mixing to form a homogenous mixture. Phase B is premixed in a separate vessel at ambient temperature and added to Phase A at 40° C. or lower temperature. Phase C is added to the now combined A and B Phases mixture in order with sufficient mixing until a homogenous cream is formed. A homogeneous and storage stable cream results.

EXAMPLE 2

A cosmetic cream in which the fish spawn protein isolate and a natural product extract are components of Phase A is provided instead of the fish spawn protein isolate and the natural product extract present in a separate Phase C per Example 1. With Phase A being formed at ambient temperature to avoid protein denaturation, a like cream is obtained.

COMPARATIVE EXAMPLES

A composition comparative to Example 1 is created as a cream absent fish spawn isolate (comparative Example A). Another composition is devoid of a natural product extract (comparative Example B). A controlled formulation lacking both fish spawn protein isolate and natural product extract is also produced (comparative Example C). A study group of 40 individuals is divided into four groups with each group applying daily a cream of Example 1 or one of comparative Examples A-C for 12 weeks. Baseline skin elasticity is measured for each subject and at study conclusion upon normalizing to the control of comparative Example C, the Example 1 composition shows superior tautness and smoothness relative to comparative Examples A-C. All compositions are standardized to at a level of from $1\times10^{-6}$ mg of the isolate and (if present) $2\times10^{-7}$ mg of the unsaturated fatty acids (if present) per square cm of skin per application.

EXAMPLE 3

Fresh, unfertilized salmon (*Salmo salar*) eggs harvested from females in reproductive phase (late fall) are kept on ice, and the extract preferably made immediately. It is possible to freeze dry eggs in a cryoprotectant (e.g., 1.5 M 1,2-propanediol and 0.2 M sucrose) without disrupting the egg membrane. Freezing should be gradual (−1° C./min) to −80° C. Eggs should be thawed and kept on ice throughout the extract preparation procedure.

Eggs are washed twice in HBSS or seawater with protease inhibitors (10 μg/ml). The washing solution is removed and the eggs are lysed and homogenized in a pre-chilled Dounce glass-glass homogenator. The lysate is transferred to Beckman Ultra Clear polymer centrifuge tubes (5 ml) while avoiding transfer of egg shells, and centrifuged for 15 min at 15,000 g at 4° C. in a Beckman ultracentrifuge using SW55T1 rotor. Three fractions are thereby obtained; lipid top fraction, cytoplasmic middle fraction, and a bottom fraction containing eggshells and nucleic debris. The cytoplasmic middle fraction is the collected extract. This extract is expected to contain most cytosolic organelles including mitochondria, lysosomes and peroxisomes, should be clear and viscous, and have an orange tint. Protease inhibitors (10 μg/ml stock) are added and extracts are kept at −80° C. Mid-blastula Zebra fish embryos are collected, liquid removed and frozen to −20° C. To prepare the extract, embryos are thawed on ice, lysed and homogenized by Dounce glass-glass homogenator in a small amount of either HBSS or seawater (preferably less than 50% liquid v/v). The lysate is filtered through a sterile linen cloth and centrifuged at 5,000 g at 4° C. for 20 minutes in a SX4250 rotor using a Beckman X-22R centrifuge. The cytoplasmic extract (supernatant) is collected and protease inhibitors (10 μg/ml) are added. The extract may be Millipore filtered (0.22 micron MilliQ sterile filter). The extracts are kept at −80° C. The extract pH is measured by litmus paper, protein concentration measured by Bradford assay, and osmolarity measured by osmometer.

This general procedure is useful for the preparation of extracts from sea urchin, shrimp, fish eggs/roe or frog eggs. Briefly, roe collected from gravid female fish soon after they liberated their eggs in a spawning program (hCG hormone injected (1 ml/kg) at 6 to 8 hours before egg liberation, usually at dawn (2-4 AM), or from gravid frogs. Roe/eggs are freeze dried or frozen at −20° C. or used fresh. Roe is collected from different kinds of fish. For sea-urchin, 0.5 M KCl is injected around the mouth to evoke shedding of eggs. The extract is prepared from eggs/roe by crushing (cell cracker or dounce-homogenization) or centrifugation at different speeds to separate cytoplasm with all content, with/without egg-shells (*zona pellucida*), with/without nucleus/cytosol, with/without organelles, with/without lipids. Further fractionation can be conducted to isolate one or more of mRNA, proteins, small peptides, carbohydrates and lipids. Major components of fatty acids in the roe are oleic acid, linoleic acid, and omega-3 fatty acids.

Upon application of the above protocol for salmon egg extracts, the salmon egg extracts had a surprisingly high protein concentration varying from 100-380 mg/ml, pH between 6.4-6.8, and an osmolarity of approximately 350 mOsm. The extracts are clear and viscous and non-filterable (by 0.45 micron MilliQ filter). The protein in the extract precipitated easily upon addition of water or hydrous solutions with low buffering capacity due to the high protein content and low pH. Extracts could be neutralized to pH 7.0 by addition of alkaline (1-3 μl 1M NaOH/ml extract), whereupon dilution in water and hydrous solutions is possible. Zebra-fish extracts had a protein concentration varying from 23-26 mg/ml, pH between 6.4-6.8, and an osmolarity between 80-150 mOsm. The extracts are clear and non-viscous, filterable and diluted readily in water at all dilutions.

EXAMPLE 4

Gel filtration-purified plus affinity-purified salmon zonases may be further purified to sequence-grade purity by one final chromatographic procedure. This procedure employs a PBE94 column, with a buffer of Tris-Acetate (10 mM, pH 9.0), where subsequent elution is with a salt gradient (up to 1 M NaCl salt) in this buffer. This step itself increases the catalytic activity of the zonases by a further 7.6 fold, for an overall purification of 714 fold and with a yield of 28% from the starting material. This purification step leaves the protein identity of the zonases intact as a 28 kDa moiety. Hence, the step does not remove unrelated, major protein contaminants from the zonase preparation. The molecular weight of purified zonases is the same as observed by Western blotting technique for zonase moieties present in the hatching fluid and in the "zonase crude".

What apparently takes place in the third and final chromatographic procedure is that small, contaminating peptides are removed. These peptides appear to be oligopeptides with around a dozen residues, originating most likely from the eggshell and/or from the salmon embryo. These peptide contaminants appear to exert inhibitory effects on zonase catalysis, since their removal increases the catalytic activity of zonase. Also, their presence interferes with the first steps in the Edman-sequencing of this zonase product. The two forms of zonases seen in this third purification step bind somewhat differently to the column matrix. However, both forms have similar amino acid sequences in their N-terminal portions.

Partial amino acid sequences from CNBr-generated peptides established the zonases as a distinct proteins. Structural analysis yielded indications that zonases may have distinct catalytic and substrate-binding domains, which may account for their sensitivity to calcium-chelating agents when acting on macromolecular (physiological) substrates (binding to inhibited, hence catalysis is inhibited indirectly), and also sensitivity to serine protease-inhibitors when acting on small substrates (catalysis is directly inhibited).

EXAMPLE 5

Both zonase and leukolectin are purified from salmon hatching fluid. To improve the protein concentration of hatching fluid, salmon eggs are transferred to minimal volumes of water prior to hatching. Highly synchronous hatching can be induced by elevated (room) temperatures, or by deoxygenation (Oppen-Berntsen et al. 1990, Aquaculture, 86, pp. 417-430), which yields a small volume of highly concentrated preparation of crude zonase and associated proteins.

The initial purification of zonase involved filtration of hatched salmon eggs through cheese cloth. This filtrate may be frozen for years without significant zonase degradation, before being thawed and employed for further protein purification. This fact greatly simplifies production of a starting material for purifying salmon zonase and associated proteins, including leukolectin.

The next, optional, step involved adjusting the protein filtrate to 4M urea, to dissociate fragments of the salmon eggshell, which allowed their removal along with extraneous debris by low speed centrifugation (15,000 g; twice for 15 min). This material showed no sign of clogging columns, which is characteristic of crude materials prepared differently from what is described above. This crude protein preparation is suitable for purification by conventional chromatographic techniques.

Leukolectin from hatching fluid may be isolated together with zonase. From partially purified zonase preparations (as described above), leukolectin may be isolated by exclusion chromatography as zonase in its native form is substantially larger than Leukolectin. For a first separation, Superdex 16/60 columns are used, whereafter zonase may be removed by affinity chromatography on Benzamidine-Sepharose columns.

For large scale preparations the use of ultrafiltration is also suitable as zonase in its native form does not significantly penetrate ultra filters with size exclusion of 100 kDa unlike leukolectin.

Buffers used are millimolar Tris (e.g. 10 mM) at pH around neutrality or slightly alkaline (pH 7.5-8.5), containing 5 mM NaCl. The leukolectin protein is found to co-purify with zonase. The size of this new protein, estimated by chromatography under native conditions, is just shy of 30 kDa.

The estimated MW of the lectin is around 25-30 kDa. Estimated pI for the corresponding salmon lectin is about pH=6.5. Observed pIs (Riste, unpublished) are from pH 6.5 to 6.9 in salmon perivitelline lectins, and from pH 6.4 to 6.6 in salmon leukocytic lectins (the lectin is identified by Western blotting techniques).

EXAMPLE 6

A study to evaluate the safety and efficacy of cosmetic products in the form of a day cream and an eye cream using the formulations disclosed above during a 12 week study period. A total of 40 female subjects, ranging in age from 37 to 60 years, are selected for the study. All 40 participants completed the study.

Under the conditions of this study, the test materials identified as the day cream and eye cream, demonstrated potential to improve facial fine lines, wrinkles, hyperpigmentation, evenness of skin tone, skin clarity, skin laxity, and tactile roughness during a twelve week use period. In addition, the test materials are well tolerated and did not demonstrate a potential to cause significant dermal irritation when applied to the face.

Statistically significant improvements in Packman and Gans scores for superficial facial lines of the face and in Visual Analog Scale (VAS) scores for facial hyperpigmentation, evenness of skin tone, skin clarity, skin laxity, and tactile roughness are observed following two, six and twelve weeks of twice daily applications. No statistically significant increases in irritation (erythema, edema, dryness, stinging, burning and tight/dry feeling) from baseline are observed at any post-treatment interval.

EXAMPLE 7

A study to evaluate the effectiveness of biocide preservatives against microbial contamination in cosmetic products in the form of a day cream and eye cream using the formulations disclosed above during two 4 week study periods is performed. The methods employed are CTFA Microbiology Guidelines, Section 20, M-3, A Method for Preservation Testing of Water Miscible Personal Care Products and USP 34, Section 61, Neutralization/Removal of Antimicrobial Activity. Test organisms included *Staphylococcus aureus, Escherichia coli, Pseudomonas aeruginosa, Candida albicans, Aspergillus niger*. For category 2 products, the preservative is considered effective in the sample examined if a). The concentrations of viable bacteria demonstrate no less than a 3.0 log reduction (99.9%) from the initial count at 7 days, and no increase for the duration of the test period and b). The concentration of viable yeast and molds demonstrate no less than a 1.0 log reduction (90.0%) from the initial count at 7 days, and no increase for the duration of the test period.

Study results showed that the day cream and eye cream conformed to the acceptance criteria for category 2 products.

EXAMPLE 8

A study is conducted to determine the comedogenic potential of test materials in the form of day cream and eye cream with formulations disclosed above by assessing whether the test materials elicited microcomedones, after four weeks of repeated application under occlusive patch conditions, relative to a negative control (undosed patch). Acetylated Lanolin Alcohol served as a positive control material in order to validate the study. The tests are conducted during a 4 week study period. A total of 15 subjects, ranging in age from 22 to 45 years, are selected for the study. All 15 participants completed the study.

The evaluation of the follicular biopsy specimens collected from the test sites indicated that the test and control materials elicited average global assessment scores of 0.5 (1-24% smallish horny masses). The average ratio of microcomedones per follicle is 1% for the test materials and the negative control, and 6% for the positive control. There are no statistically significant differences in the ratios of micro comedones to follicles between the test materials and the negative control, while the positive control demonstrated a significantly greater ratio than the negative control.

The study showed there are no adverse experiences reported during the study period. The test materials did not demonstrate a potential to elicit comedogenicity. The ratios of micro comedones per follicle are not statistically different for sites treated with each of the test materials and sites to which an untreated negative control patch is applied.

EXAMPLE 9

A study is conducted to determine the dermal irritation and sensitization potential of a test material in the form of eye cream with formulations disclosed above. Tests are conducted during a 8 week study period. This study is initiated with 225 subjects. Eleven subject discontinued study participation for reasons unrelated to the test material. A total of 214 subjects completed the study.

The tests are conducted by applying patches with the test material to a test area is wiped with 70% isopropyl alcohol and allowed to dry. The test material is applied to the upper back (between the scapulae) and is allowed to remain in direct skin contact for a period of 24 hours. Patches are applied to the same site on Monday, Wednesday, and Friday for a total of 9 applications during the Induction Period. This schedule may have been modified to allow for missed visits or holidays. If a subject is unable to report on an assigned test date, the test material is applied on 2 consecutive days during the Induction Phase and/or a makeup day is added at the end of the Induction Phase. The sites are graded by a proctoring technician for dermal irritation 24 hours after removal of the patches by the subjects on Tuesday and Thursday and 48 hours after removal of the patches on Saturday, unless the patching schedule is altered as described above.

The sites are graded according to the following scoring system:
Dermal Scoring Scale
0 No visible skin reaction
± Barely perceptible erythema
1+Mild erythema
2+Well defined erythema
3+Severe erythema and edema
4+Erythema and edema with vesiculation
If a "2+" reaction or greater occurred, the test material is applied to an adjacent virgin site. If a "2+" reaction or greater occurred on the new site, the subject is not patched again during the Induction Phase but is challenged on the appropriate day of the study. At the discretion of the Study Director, patch sites with scores less than a "2+" may have been changed.

Following approximately a 2-week rest period, the challenge patches are applied to previously untreated test sites on the back. After 24 hours, the patches are removed by a CRL technician and the test sites are evaluated for dermal reactions. The test sites are re-evaluated at 48 and 72 hours. Subjects exhibiting reactions during the Challenge Phase of the study may have been asked to return for a 96-hour reading.

Based on the test population of 214 subjects and under the conditions of this study, the eye cream test material did not demonstrate a potential for eliciting dermal irritation or sensitization.

EXAMPLE 10

A series of studies are conducted to determine the dermal irritation and sensitization potential of a test material in the form of day cream and eye cream with formulations disclosed above with additional sun protection factor (SPF) component added to the formulations. A SPF is defined as the ratio of the amount of energy required to produce minimal erythema on protected skin to the amount of energy needed to produce minimal erythema on untreated skin calculated as follows:

$$SPF = \frac{MED \text{ Protected Skin } J/m^2 \; MED}{\text{Unprotected Control Site } J/m^2}$$

I. A study is conducted to evaluate the efficacy of a sunscreen product combined with a day cream as formulated above by determining the sun protection factor (SPF) using the International Sun Protection Factor (SPF) Test Method (May 2006) under static conditions. A standard sunscreen formulation is tested concurrently with the test material. The standard is Padimate O/Oxybenzone SPF Standard (COLIPA P2) (16.63±3.43). The location of test/control material application is to the back and is randomized such that the area of the back receiving treatment with an individual test material is not the same for all subjects. A total of 10 male and female subjects, ranging in age from 25 to 57 years and in generally good health, are selected for the study. There are no adverse events reported during the course of the study.

II. A study is conducted to evaluate the efficacy of a sunscreen product with an SPF 30 combined with a day cream as formulated above by determining the ultraviolet A (UVA) Protection Factor (PFA) under static conditions according to the Japan Cosmetic Industry Association (JCIA) Measurement Standard for UVA Protection (01/01196). A total of 10 adult subjects took part in the study. A Xenon Arc Multi-Port Solar Simulator (150 w, Model 15S, Solar Light Company, Philadelphia, Pa.) which has a continuous emission spectrum of ultraviolet light in the UVA and UVB region (290-400 nm), is used as a source of ultraviolet light irradiation and filtered to provide a basic solar-like spectrum. The following filters are employed to ensure the proper spectral outputs: Schott WG33513 mm and UG1111 mm. The lamp output is measured immediately prior to the start of each subject's testing with an UV Intensity Meter (Model PMA2100, Solar Light Company, Philadelphia, Pa.). The spectral distributions of the optical output of the solar simulators are validated annually.

Pigment Darkening is a brown-gray to brown black reaction observed in human skin after UVA exposure due to a photo-oxidation reaction in which a colorless melanin precursor is oxidized to become pigmented melanin. A Minimal Persistent Pigment Darkening (MPPD) is defined as the dose of UVA light irradiation necessary for inducing such a response in untreated skin. Prior to the testing phase, the MPPD of each subject is determined by a progressive geometric sequence of UV light exposures. The dose increment of UVA radiation is 1.25. Two to four hours after irradiation, the sites are evaluated for pigment darkening according to the following scoring system:

0 Negative, No visible reaction
± Barely perceptible (minimal) pigment darkening
1+ Unequivocal (moderate) pigment darkening distinct borders
2+ Pronounced or well-defined pigment darkening Test sites measuring 5×10 cm are outlined with a surgical marking pen on the subject's back between the scapulae and the beltline, lateral to the midline. These areas are designated for the test material or standard sunscreen. An adjacent site is designated for a concurrent MPPD determination on untreated skin. After product application, each test area is subdivided into approximately 1-cm$^2$ sites that are used for defined serial UVA light exposure. A 0.1 ml portion of test material or standard is applied to the appropriate test site and spread evenly over the site using a fingercot (equivalent to 2 μl/cm2). Irradiation of the sites began between 15 minutes and 30 minutes after application. Exposure times are selected for each treated site based upon the previously determined MPPD of unprotected skin and the anticipated PFA of the test material or standard. All test sites are evaluated two to four hours after exposure to determine minimal persistent pigment darkening response.

A Protection Factor of UVA (PFA) is defined as the ratio of the amount of time required to produce an MPPD on protected skin to the amount of time needed to produce an MPPD on untreated skin calculated as follows:

$$PFA = \frac{MPPD \text{ Protected Skin } MPPD}{\text{Unprotected Control Site}}$$

Standard error must lie within 10% of the measured values.

The integer of the average PFA value of treated irradiated sites determines the protection grade of UVA. For all PFA values equivalent to 2 or greater, the following classification is applied to determine the protection grade:

| PFA Value | PA (Protection Grade of UVA) |
|---|---|
| 2 or more but less than 4 | PA+ |
| 4 or more but less than 8 | PA++ |
| 8 or more | PA+++ |

The submitted test material Day Cream with SPF 30 exhibited an average UVA Protection Value of PFA 6.5, in the 10 subjects.

III. A study is conducted to evaluate a test material of a day cream as formulated above containing sunscreen actives for broad spectrum protection by determining its critical wavelength in compliance with the FDA (Federal Register/Vol 76, No 117/Friday, Jun. 17, 2011/Rules and Regulations).

The absorbance of a sunscreen is integrated (summed) from 290 nm across the UV wavelengths until the sum reaches 90% of the total absorbance of the sunscreen in the ultraviolet region (290-400 nm). The wavelength at which the summed absorbance reaches 90% of total absorbance is defined as the 'critical wavelength' and is considered to be a measure of the breadth of sunscreen protection. A sunscreen having a significant part of their absorbance in the UVA can be classified as 'broad spectrum', when the critical wavelength is longer than 370 nm.

Spectral transmittance for each wavelength over the full UV spectrum (290 to 400 nanometers) is determined. The transmittance values are measured at 1 nanometer intervals.

The Critical Wavelength of the test material day cream with SPF is 371.00 nm, which satisfies the Critical Wavelength criteria of a minimum of 370 nm required for "Broad Spectrum" labeling.

A similar test study is conducted to evaluate a test material day cream as formulated above containing sunscreen actives for broad spectrum protection by determining its in vitro UVA protection factor (UVA-PF), its SPF/UVA-PF ratio and the day cream critical wavelength is found to be in compliance with the COLIPA Guidelines, 2011.

Any patents or publications mentioned in this specification are herein incorporated by reference to the same extent as if each individual publication was specifically and individually indicated to be incorporated by reference.

The foregoing description is illustrative of particular embodiments of the invention, but is not meant to be a limitation upon the practice thereof.

The invention claimed is:

1. A cosmetic comprising an emulsion that comprises:
   a fish spawn protein isolate obtained from hatching fish eggs, wherein the isolate comprises an active protein that constitutes from $1\times10^{-8}$ to $1\times10^{-5}$ total weight percent of the cosmetic;
   a natural product extract present from 0.001 to 10 total weight percent and comprising unsaturated fatty acids and sterols, said natural product extract having antioxidant activity on mammalian skin; and
   an emulsifier, a solubilizer, or a combination thereof.

2. The cosmetic of claim 1, wherein said natural product extract is an algae extract or an extract from plant leaves, stems, buds, roots, or a combination thereof.

3. The cosmetic of claim 1, wherein said active protein is zonase.

4. The cosmetic of claim 1, further comprising ascorbic acid 2-glucoside or ascorbate salt.

5. The cosmetic of claim 1, wherein said cosmetic is substantially free of silicone, petrolatum, synthetic paraben, and mineral oil.

6. The cosmetic of claim 1, wherein said active protein consists essentially of zonase.

7. The cosmetic of claim 1, wherein said fish spawn protein isolate comprises active leukolectin.

8. The cosmetic of claim 1, wherein said active protein consists essentially of leukolectin.

9. The cosmetic of claim 1, wherein said fish eggs are salmon eggs.

10. The cosmetic of claim 1, wherein said fish eggs are eggs from at least one of whitefish, vendace, cod, capelin, and burbot.

11. A cosmetic comprising an emulsion that comprises:
    a fish egg hatching protein isolate obtained from hatching fish eggs and comprising an active protein that constitutes from $1\times10^{-8}$ to $1\times10^{-5}$ total weight percent of the cosmetic;
    at least one biocide; and
    an emulsifier, a solubilizer, or a combination, wherein the emulsion has an aqueous phase having a pH of between 5.6 and 7.9.

12. The cosmetic of claim 11, wherein the cosmetic is substantially free of silicone, petrolatum, synthetic paraben, and mineral oil.

13. The cosmetic of claim 11, wherein said at least one biocide (a) comprises Japanese honeysuckle extract in combination with another plant extract, and (b) inhibits growth of a microorganism selected from Gram positive bacteria, Gram negative bacteria, and fungi.

14. The cosmetic of claim 11 further comprising a natural product extract including unsaturated fatty acids and sterols.

15. The cosmetic of claim 14, wherein said extract is derived from red algae, brown algae or tuft-forming cyanobacteria.

16. The cosmetic of claim 11, wherein the cosmetic further comprises ascorbic acid 2-glucoside or an ascorbate salt.

17. The cosmetic of claim 15, wherein said cosmetic is substantially free of silicone, petrolatum, synthetic paraben, and mineral oil.

18. The cosmetic of claim 11, wherein said active protein is zonase.

19. The cosmetic of claim 11, wherein said active protein is leukolectin.

20. The cosmetic of claim 11, wherein said at least one biocide comprises a natural product extract.

21. A cosmetic comprising an emulsion that comprises:
    a fish spawn protein isolate obtained from hatching fish eggs and comprising an active protein that constitutes from $1\times10^{-8}$ to $1\times10^{-5}$ total weight percent of the cosmetic;
    at least one biocide;
    and an emulsifier, a solubilizer, or a combination thereof, wherein, on average, in a test population of human subjects, application of the cosmetic to each subject's facial skin does not produce dermal irritation.

22. The cosmetic of claim 21, wherein said emulsion has an aqueous phase having a pH between 5.6 and 7.9.

23. The cosmetic of claim 21, wherein said active protein is zonase or leukolectin.

* * * * *

UNITED STATES PATENT AND TRADEMARK OFFICE
CERTIFICATE OF CORRECTION

PATENT NO. : 8,992,996 B2  
APPLICATION NO. : 13/904501  
DATED : March 31, 2015  
INVENTOR(S) : Enrique P. Alabata and Patricia S. Pao Page 1 of 1

It is certified that error appears in the above-identified patent and that said Letters Patent is hereby corrected as shown below:

In the claims

Column 18, Line 22: In Claim 11, delete "combination," and insert therefor -- combination thereof, --.

Column 18, Line 54: In Claim 21, after "biocide;", insert -- and --.

Column 18, Line 55: In Claim 21, before "an", delete "and".

Signed and Sealed this  
Fourteenth Day of June, 2016

Michelle K. Lee  
*Director of the United States Patent and Trademark Office*